United States Patent [19]

Romine et al.

[11] Patent Number: 5,380,854
[45] Date of Patent: Jan. 10, 1995

[54] DIPHENYL-HETEROCYCLIC-OXAZOLE AS PLATELET AGGREGATION INHIBITORS

[75] Inventors: Jeffrey L. Romine, Meriden; Nicholas A. Meanwell, East Hampton; Scott W. Martin, Middletown, all of Conn.

[73] Assignee: Bristol-Myers Squibb Company, New York, N.Y.

[21] Appl. No.: 92,402

[22] Filed: Jul. 14, 1993

Related U.S. Application Data

[62] Division of Ser. No. 862,680, Apr. 3, 1992, Pat. No. 5,254,576.

[51] Int. Cl.[6] .................................. C07D 263/34
[52] U.S. Cl. ........................... 548/235; 548/236
[58] Field of Search ........................ 548/235, 236

[56] References Cited

U.S. PATENT DOCUMENTS 4,460,598 7/1984 Lautenschläger et al. ......... 548/336

FOREIGN PATENT DOCUMENTS 0434034 6/1991 European Pat. Off. .

OTHER PUBLICATIONS

Lautenschlager, et al., *Drugs of the Future*, 11, 26 (1986).
Moncoda, et al., *Nature*, 263, 663 (1976).
Nickolson, et al., *Med. Res. Rev.*, 5, 1 (1985).
Seiler, et al., *J. Pharmacol. Exp. Ther.*, 255: 1021 (1990).
T. Shioiri, Y. Hamada, *Heterocycles*, 27: 1035: (1988).
Waserman, et al., *Chem. Rev.*, 86: 845 (1986).
J. L. Kraus, *Synth. Comm.*, 16: 827 (1986).
J. F. W. McOmie, M. L. Watts, *Chem. Ind.*, 1658 (1963).
Negishi et al., *J. Org. Chem.*, 42: 1821 (1977).
Wasserman, et al., *Tetrahedron Lett.*, 22: 1737 (1981).
R. F. Abdulla, R. S. Brinkmeyer, *Tetrahedron*, 35: 1675 (1979).
A. P. Kozikowski, A. J. Ames, *J. Org. Chem.*, 45: 2548 (1980).
Moriya, et al., *J. Med. Chem.*, 29: 333 (1986).
D. Hoppe, *Angew. Chem., Int. Ed.*, 13: 789 (1974).

(List continued on next page.)

*Primary Examiner*—Robert Gerstl
*Attorney, Agent, or Firm*—Prabodh I. Almaula

[57] ABSTRACT

A novel series of oxazole derivatives having enhanced water solubility bioavailability and metabolic stability is disclosed in the Formula I

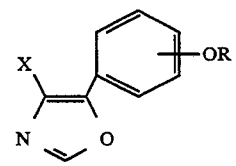

X is 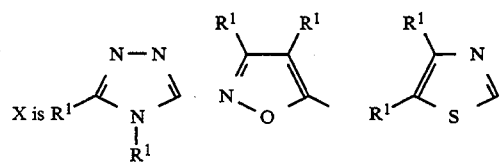

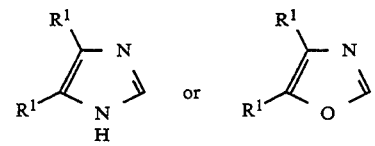

R is $CH_2R^2$, H;
$R^1$ is Ph or Th;
$R^2$ is

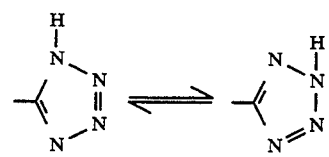

H, CN, $CO_2R^3$, or $OR^3$; and
$R^3$ is H, or $C_1$-$C_4$ lower alkyl;

or pharmaceutically acceptable salt thereof.

3 Claims, No Drawings

OTHER PUBLICATIONS

J. Frump, *Chem. Rev.*, 71: 483 (1971).
H. Eckert, B. Forster, *Angew. Chem., Int. Ed.*, 26: 894 (1987).
Suzuki, et al., *J. Org. Chem.*, 38: 3571–3575 (1973).
H. Reimlinger, *Chemistry and Industry*, 1082–1083 (1970).
Davidson, et al., *J. Org. Chem.*, 2: 319 (1937).
I. Yamawaki, K. Ogawa, *Chem. Pharm. Bull.*, 36: 3142 (1988).
Meanwell, et al., *J. Of Med. Chem.*, 35: 389–397 (1992).
Merritt, et al., *Br. J. Pharmacol.*, 102: 251–259 (1991).
Merritt, et al., *Br. J. Pharmacol.*, 102: 260–266 (1991).
Ozaki, Chem Pharm Bull, 31 (12) 4417 (1983).

DIPHENYL-HETEROCYCLIC-OXAZOLE AS PLATELET AGGREGATION INHIBITORS

This application is a division, of application Ser. No. 07/862,680, filed Apr. 3, 1992 now U.S. Pat. No. 5,254,576.

BACKGROUND OF THE INVENTION

1. Field of the Invention

This invention relates to a series of novel oxazole derivatives which are useful as inhibitors of ADP-induced aggregation of human blood platelets in platelet-rich-plasma.

2. Description of the Art

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischemic heart disease, atherosclerosis, multiple sclerosis, indracranial tumors, thromboembolism, and hyperlipemia (A. Poplawski, et al, *J. Atherosclerosis Research*, 8: 721 (1968)).

Octimibate (1) has been revealed to be a broad spectrum inhibitor of platelet aggregation; $IC_{50}=1$ μg/ml (human PRP vs ADP). (U.S. Pat. No. 4,460,598; Lautenschlager, et al *Drugs of the Future*, 11, 26 (1986)).

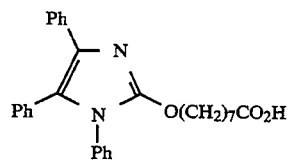

(1)

EPO 0434034, to Meanwell, et al., discloses (2), which is an orally active broad spectrum inhibitor of platelet aggregation.

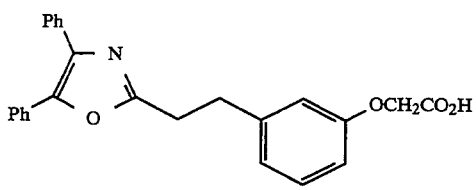

(2)

SUMMARY OF THE INVENTION

The present invention provides novel oxazole derivatives having Formual I, infra. or pharmaceutically acceptable salt thereof, which have enhanced potency and aqueous activity.

The compounds of Formula I are useful as inhibitors of adenosine diphosphate-induced aggregation of human blood platelets in platelet rich plasma.

Another embodiment of the invention concerns pharmaceutical compositions comprised of a Formula I compound combined with at least one pharmaceutically acceptable excipient.

Yet another embodiment relates to a method for inhibiting blood platelet aggregation in a mammal which comprises administering a therapeutically effective amount of a compound of Formula I to a mammal in need of such treatment.

DETAILED DESCRIPTION OF THE INVENTION

The compounds of the instant invention comprise those of Formula I

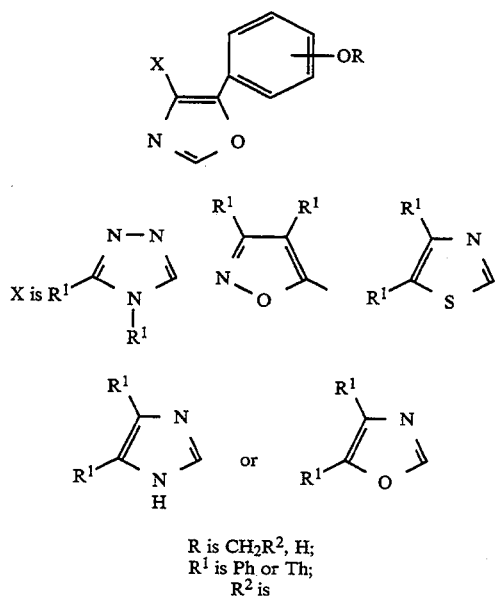

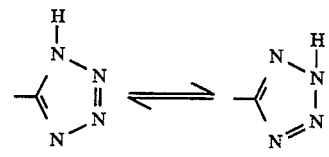

$R$ is $CH_2R^2$, H;
$R^1$ is Ph or Th;
$R^2$ is

H, CN, $CO_2R^3$, or $OR^3$; and
$R^3$ is H, or $C_1$-$C_4$ lower alkyl;

H, CN, $CO_2R^3$, $OR^3$; and $R^3$ is H, or $C_1$-$C_4$ lower alkyl;

or pharmaceutically acceptable salt thereof.

It is understood that as used herein limitation of Formula I are defined as follows:

The term "$C_1$-$C_4$ lower alkyl" refers to a branched or unbranched saturated hydrocarbon chain containing from 1 to 4 carbon atoms, for example, methyl, ethyl, n-propyl, isopropyl, butyl, and isobutyl.

The symbol "Ph" represents phenyl. The symbol "Th" represents thiophene.

According to the present invention, the compounds characterized by Formula I and the pharmaceutically acceptable acid addition salts thereof, were prepared as outlined in Scheme I.

Condensation of an isonitrile with an activated benzoate derivative was used to yield compound 5. (T. Shioiri, Y. Hamada, *Heterocycles*, 27, 1035 (1988)). This route generated the final target in a convergent approach from a series of aryloxy esters (3), available in two steps from commercially available 3-hydroxybenzaldehyde, and the diaryl oxazole (4) (Scheme I).

Benzoin (1) was coupled to carbobenzyloxy glycine and cyclized to give the protected aminomethyl oxazole (2). (H. H. Wasserman, K. S. Prowse, K. E. McCarthy, *Chem. Rev.*, 86, 845 (1986)). Deprotection, formylation, and dehydration under standard conditions (G. D. Hartman, L. M. Weinstock, *Org. Syn*, VI, 620) gave the isonitrile (4). Condensation of (3) and (4), upon activation with diphenylphosphoryl azide in the presence of base, gave the corresponding products 6–12 (Table 1). Compound 5, was obtained by hydrolysis of methyl ester (6) in lithium hydroxide/dimethoxyethane solution, and the tetrazole (12) was prepared from the reaction of 11 with tri-n-butyltin azide. (J. L. Kraus, *Synth. Comm.*, 16, 827 (1986)).

TABLE 1-continued

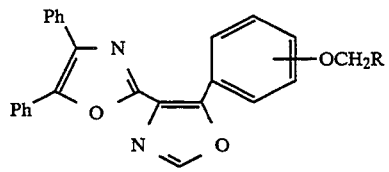

| Compound # | Ring Position | R |
|---|---|---|
| 9 | meta | $CO_2Et$ |
| 10 | meta | $OCH_3$ |
| 11 | meta | CN |
| 12 | meta | |

SCHEME I

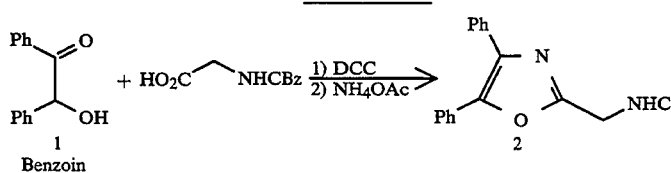

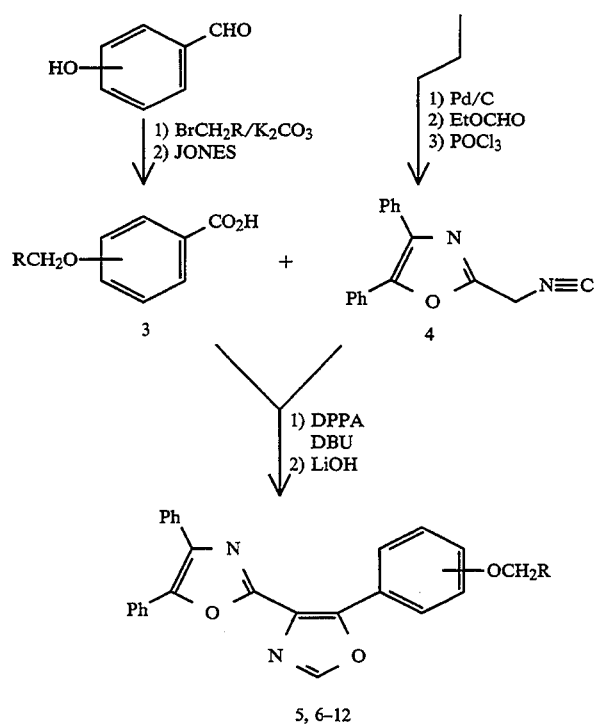

5, 6-12

TABLE 1

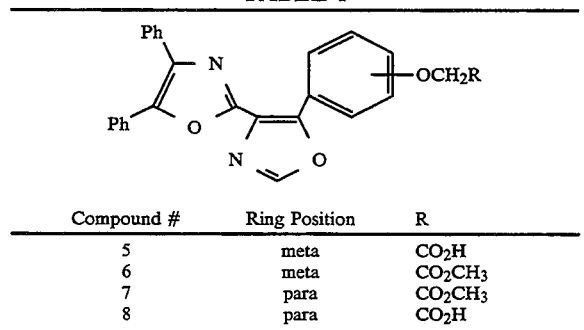

| Compound # | Ring Position | R |
|---|---|---|
| 5 | meta | $CO_2H$ |
| 6 | meta | $CO_2CH_3$ |
| 7 | para | $CO_2CH_3$ |
| 8 | para | $CO_2H$ |

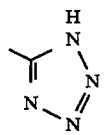

Analogs of the diphenyl oxazole ring were prepared from a common intermediate (13), which allowed suitable elaboration of various diaryl heterocycles. Glycine was esterfied with benzyl alcohol, formulated, and dehydrated to afford isonitrile (14). This material was treated with base and acid chloride (15). The resulting diester was selectively cleaved upon hydrogenation to yield compound (13) (Scheme II).

SCHEME II

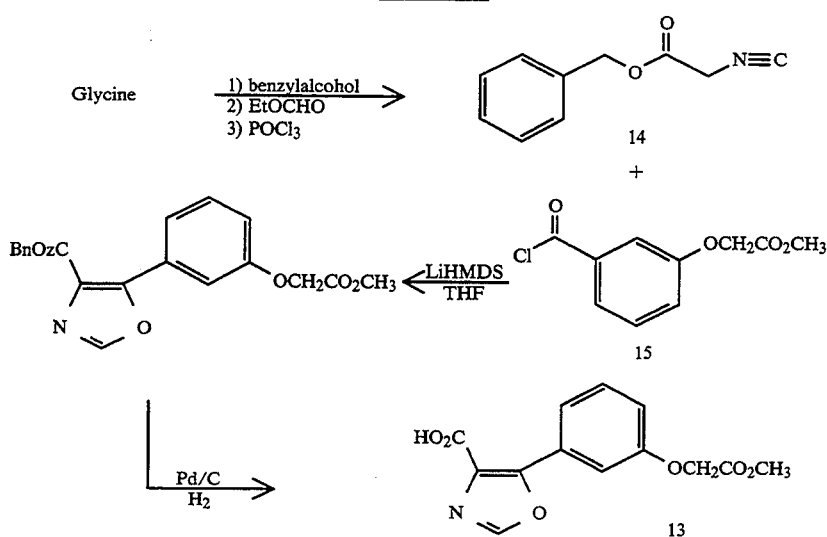

Scheme III depicts the synthetic approaches to a series of heterocycles from (13) (Table 2). N-phenol benzamidrazone was coupled with (13) and heated to cyclize to the triazole ring system (16) and (17). (H. Reimlinger, W. R. F. Lingier, J. M. Vandewalle, Chem. Ber., 104, 639 (1971)). Acylation of benzoin bisthiophene derivative (18) before exposure to ammonium acetate/acetic acid solution at reflux gave the bis-thiophene oxazoles (19) and (20). The acid (13) was activated as an acid chloride, and reduced to aldehyde (21) (Pd/C, $H_2$) before being stirred together with benzil and ammonia to give imidazoles (22) and (23). (D. Davidson, M. Weiss, M. Jelling, J. Org. Chem., 2, 319 (1937)).

An additional two heterocycles were prepared as outlined in Scheme IV. The phenyl oxazole (24) was added to the dianion of deoxybenzoin oxime and cyclized with mild acid. (I. Yamawaki, K. Ogawa, Chem. Pharm. Bull., 36, 3142 (1988)). Deprotection, alkylation, and hydrolysis gave diphenyl isoxazoles (26) and (27). Subjection of (24) to ammonia in a Parr bomb gave amide (28). Compound (28) was converted to (29) (J. F. W. McOmie, M. L. Watts, Chem. Ind., 1658 (1963)) and ensuing thiolation and cyclization gave rise to silyl ether (30). Deprotection of the phenol with fluoride ion and alkylation with methyl bromoacetate delivered thiazoles (31) and (32).

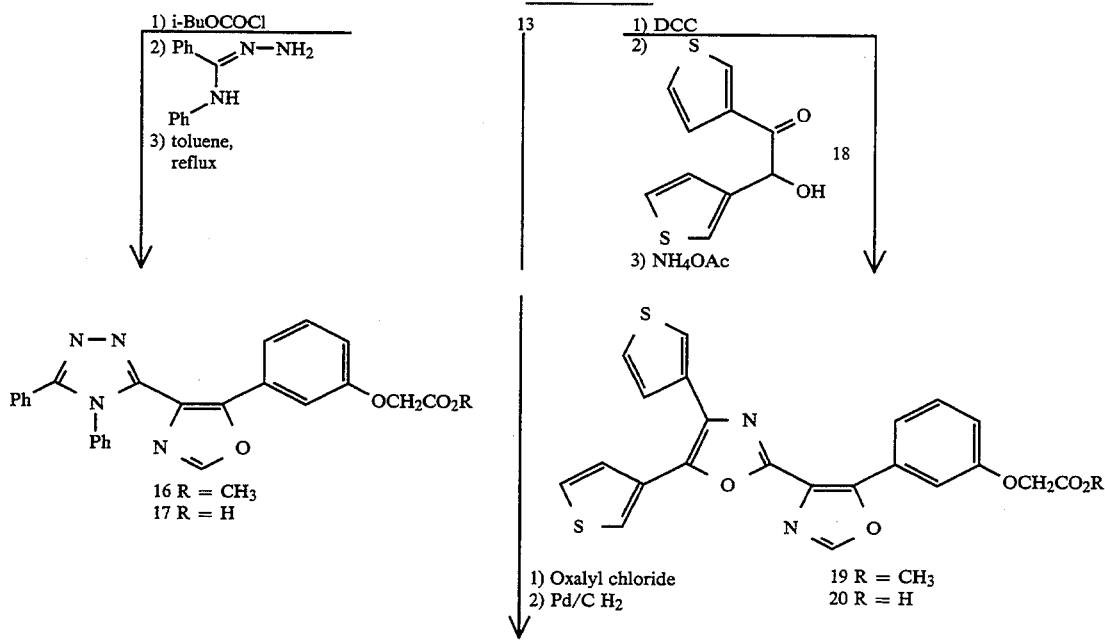

-continued
Scheme III
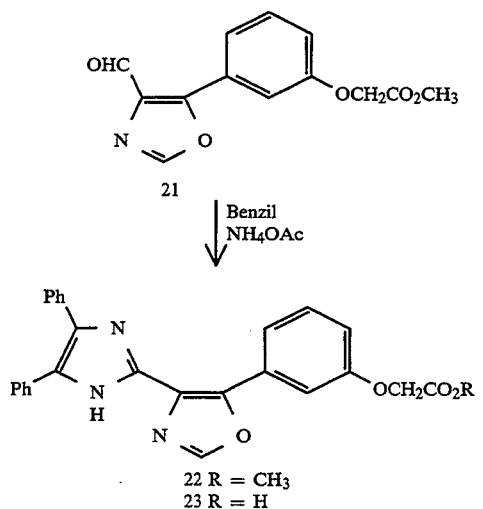
Scheme IV
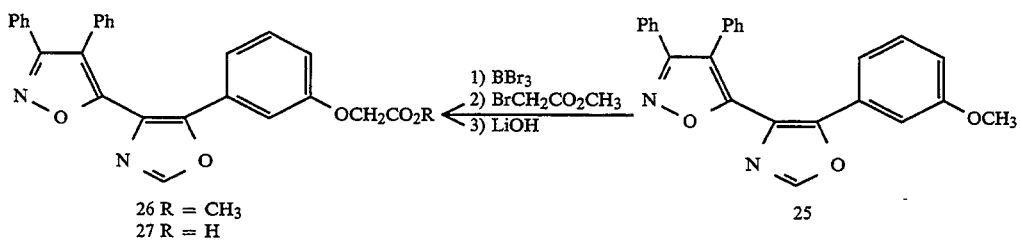
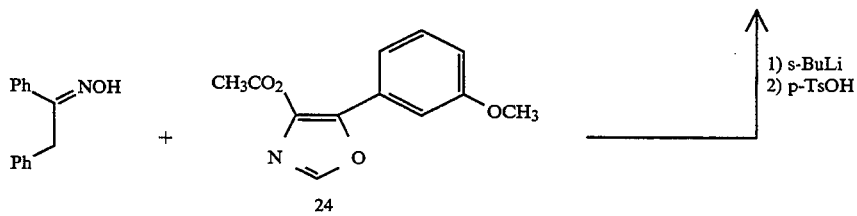
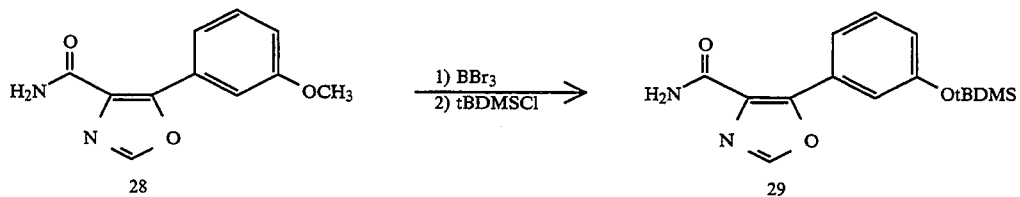
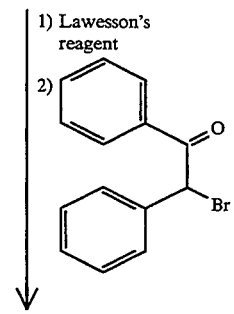

-continued
Scheme IV

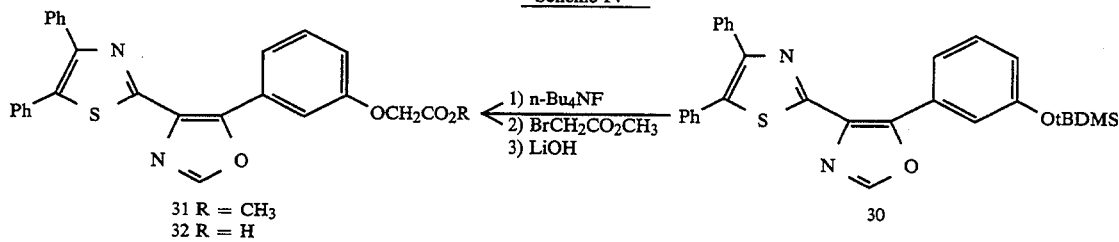

31 R = CH₃
32 R = H

TABLE 2

Vitro Inhibition of Human Platelet Aggregation

| Compound # | Diphenyl Ring | R |
|---|---|---|
| 16 | N—N (Ph, N-Ph) | CO₂CH₃ |
| 17 | | CO₂H |
| 19 | Th, Th, N, O | CO₂CH₃ |
| 20 | | CO₂H |
| 22 | Ph, Ph, N, NH | CO₂CH₃ |
| 23 | | CO₂H |
| 26 | Ph, Ph, N, O | CO₂CH₃ |
| 27 | | CO₂H |
| 31 | Ph, Ph, N, S | CO₂CH₃ |
| 32 | | CO₂H |

The aggregometer method of Born, G. V .R., J. Physiol., (London), 162, 67–68, (1962) as modified by Mustard, J. F., et al., J. Lab. Clin. Med., 64, 548–599, (1964) was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube containing 3.8% sodium citrate to prevent clotting (1 part citrate to 9 parts blood).

Platelet rich plasma (PRP) was separated by centrifugation for 10 minutes at 1000 rpm (140 xg) from citrated (3.8%) human blood. All glassware used for preparation of PRP is silicon treated. ADP in final concentration of 0.5 mcg/mL or 0.05 mL of a collagen suspension prepared according to the method described by Evans, G., et al., J. Exp. Med., 128, 877–894, (1968) was used to induce aggregation. The various compounds tested were dissolved in dimethylsulfoxide (DMSO) so that 5 mol added to the platelet rich plasma would yield the desired test concentration. Vehicle control trials were done and compared with aggregation induced in platelet rich plasma containing various concentrations of the test compounds. Dose response curves were obtained and Inhibitor Concentration ($IC_{50}$) values calculated. In this test, the $IC_{50}$ values for dipyridamole, a clinically useful antithrombogenic agent, are 512 mcg/ml vs. ADP and 245 mcg/ml vs collagen. Results for 50% inhibition of ADP-induced aggregation are given hereinafter.

The target compounds were evaluated as inhibitors of ADP-induced aggregation of human blood platelet in platelet-rich-plasma (PRP) in vitro. The test compounds were incubated at about 37° C. in PRP for about 3 minutes prior to the addition of sufficient ADP to provide a final ADP concentration of 5.86 mM.

TABLE 3

| Compound | $IC_{50}$ μg/ml (human PRP vs ADP) |
|---|---|
| 6 | 0.012 |
| 5 | 0.012 |
| 7 | 32 (51%) |
| 8 | 32 (44%) |
| 9 | — |
| 10 | 28 |
| 11 | 32 (14%) |
| 12 | 0.06 |
| 16 | >32 |
| 17 | >32 |
| 19 | 0.19 |
| 20 | 0.21 |
| 22 | 0.13 |
| 23 | 0.012 |
| 26 | 32 (27%) |
| 27 | 32 (36%) |
| 31 | 0.26 |
| 32 | 0.096 |

The Formula I compounds or pharmaceutically acceptable salts thereof have pharmacological properties which make them particularly useful as inhibitors of ADP-induced aggregation of human blood platelets in platelet rich plasma.

Another embodiment of the invention concerns pharmaceutical compositions comprised of a Formula I compound combined with at least one pharmaceutically acceptable excipient. Yet another embodiment relates to a method for inhibiting blood platelet aggregation in a mammal which comprises administering a therapeutically effective amount of a compound of Formula I to a mammal in need of such treatment.

The dosage employed in the instant therapeutic methods will vary with the form of administration, the particular compound chosen, the subject being tested and the effect desired. Suitable effective doses in animals range from 0.01 to 50 mg/Kg body weight orally and from 0.001 to 20 mg/kg body weight parenterally (generally characterized as subcutaneous, intramuscular, and intravenous injection). It is contemplated that the effective unit dose in man will range from 0.1 to 50 mg/Kg and preferably from 0.5 to 30 mg/Kg administered one to three times a day. In accordance with conventional clinical practice, the effective dose can be determined by administering a Formula I compound at a dosage substantially less than the dose of the compound which is thought to be effective and then increasing the dosage in small increments until the desired effect is achieved.

In carrying out the instant therapeutic methods, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectable compositions are formulated as known in the art and may contain appropriate dispersing or wetting agents and suspending agents identical or similar to those mentioned above.

All publications cited in this specification are indicative of the level of skill of those skilled in the art to which this invention pertains. Each publication is individually incorporated herein by reference in the location where it is cited.

The compounds which constitute the invention and their methods of preparation will appear more fully from a consideration of the following examples. The compounds which are not shown by specific example are readily prepared by analogous procedure. The following examples are given by way of illustration and are not to be construed as limiting the invention in any way inasmuch as many variations of the invention are possible within the spirit of the invention.

All temperatures are degrees Centigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

4,5-Diphenyl-2-oxazolyl-methylformamide

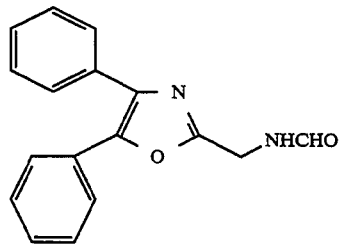

Compound (2) benzyl [(4,5-diphenyl-2-oxazolyl)methyl]carbamate (56 g, 0.15 mol) was added to a suspension of 10% palladium on carbon (16 g) in 1.5 L of 5% solution formic acid in methanol. The reaction mixture was stirred about 18 hours, filtered through a celite pad, and concentrated. The residual oil was taken up in toluene (500 mL) and ethyl formate (100) and heated at about 70° C. for about 2.5 hours. After being diluted with ethyl acetate (1 vol) the solution was washed with saturated sodium bicarbonate solution, brine, and dried ($Na_2SO_4$). Concentrated gave 38 g (94%) of product. IR (KBr, cm$^{-1}$) 3288, 1658, 1502, 1366, 1206, 1062, 766, 694. $^1$H NMR (300 MHz, CDCl$_3$) δ4.66 (2H, d, J=5.5H$_3$), 6.90 (1H, brs), 7.28 to 7.38 (6H, m), 7.50 to 7.62 (4H, m), 8.26 (1H, s); $^{13}$C NMR (75 MH$_z$, CDCl$_3$) ppm 35.43, 126.53, 126.58, 127.81, 127.90, 128.34, 128.41, 128.70, 128.72, 128.86, 128.98, 131.92, 135.09, 146.29, 158.81, 161.15; m/e 279 (MH$^+$).

Anal. Calcd for $C_{17}H_{14}N_2O_2$: C, 73.37; H, 5.07; N, 10.07.

Found: C, 73.19; H, 4.90; N, 10.14.

EXAMPLE 2

4,5-Diphenyl-2-oxazolyl-methylisocyanide, (4)

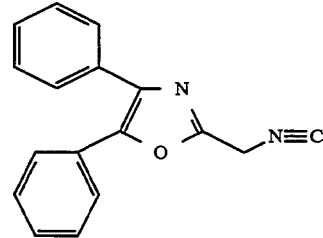

4,5-Diphenyl-2-oxazolyl-methylformamide (14 g, 0.05 mol) was dissolved in dichloromethane (70 mL) /triethylamine (16 mL) and cooled to about 0° C. under N$_2$. Upon dropwise addition of phosphorous oxychloride (4.7 mL, 0.05 mol), the reaction mixture was warmed to about 25° C. and stirred about 1 hour. A 40% sodium carbonate solution (50 mL) was added and after about 15 minutes the reaction mixture was diluted with water (1 vol), extracted with dichloromethane, washed with saturated sodium carbonate solution, brine and dried ($Na_2SO_4$) to give 13 g (98%) of 4 as a white solid. Recrystallization from ether gave light amber colored crystals, mp 95°–96° C. IR (KBr, cm$^{-1}$) 2970, 2956, 2160 (NC), 1604, 1594, 1502, 1446, 1338, 1212, 1054, 1026, 954, 916, 778, 764, 712, 694, 674, 654, 526. $^1$H NMR (300 MHz, CDCl$_3$) δ4.81 (2H, s), 7.31 to 7.41 (7H, m), 7.57 to 7.66 (5H, m). $^{13}$C NMR (75 MHz, CDCl$_3$) ppm 39.03, 126.78, 127.86, 128.04, 128.58, 128.73, 128.83, 129.25, 131.53, 135.77, 147.28, 153.17, 160.84. m/e 261 (MH+).

Anal. Calcd. for C$_{17}$H$_{14}$N$_2$O: C, 78.44; H, 4.65; N, 10.76.

Found: C, 78.38; H, 4.56; N, 10.74.

EXAMPLE 3

Methyl[3-[4,5-diphenyl-2-oxazolyl)-5-oxazolyl]phenoxy]acetate, (6)

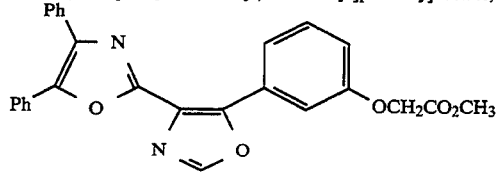

To a mixture of 4,5-diphenyl-2-oxazolyl-methylisocyanide (4) (2.8 g, 11 mmol), 3-(methoxycarbonyl)methoxy]benzoic acid (2.3 g, 11 mmol), and DBN (5 mL, 33.5 mmol) dissolved in DMF (100 mL), was added DPPA (2.5 mL, 11 mmol) by dropwise addition. The reaction mixture was stirred about 18 hours and diluted with sodium bicarbonate solution (1 vol), and extracted with ethyl acetate/ether (1:1). The organic phase was washed with water and brine before drying over MgSO$_4$. Concentration and recrystallization gave 6, 4 g (83%), mp 116°–117° C. IR (KBr, cm$^{-1}$) 3460, 1738, 1585, 1445, 1300, 1065, 765, 695. $^1$H NMR (300 MHz, CDCl$_3$) δ3.73 (3H, s), 4.66 (2H, s), 7.03 (1H, dd, J=8.2 Hz, J=2.5 Hz), 7.30 to 7.43 (7H, m), 7.66 to 7.75 (4H, m), 7.88 (1H, d, J=7.8 Hz), 7.99 (1H, s), 8.32 (1H, Br. s). $^{13}$C NMR (75 MHz, CDCl$_3$) ppm 52.06, 65.22, 113.15, 117.03, 12.52, 124.25, 126.75, 126.98, 128.15, 128.29, 128.48, 128.56, 128.74, 129.67, 132.12, 136.31, 149.64, 149.79, 154.08, 157.72, 168.92. m/e 453 (MH+).

Anal. Calcd. for C$_{27}$H$_{20}$N$_2$O$_5$: C, 71.67; H, 4.46; N, 6.19

Found: C, 71.58; H, 4.29; N, 6.14

EXAMPLE 4

3-[4,5-Diphenyl-2-oxazolyl)-5-oxazolyl]phenoxy]acetic acid, (5)

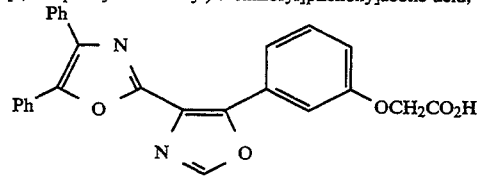

Methyl [3-[4,5-diphenyl-2-oxazolyl) -5-oxazolyl ]phenoxy]acetate (6) (3 g, 6.6 mmol) and lithium hydroxide monohydrate (560 mg, 13.3 mmol) were admixed in DME (250 mL) and heated at reflux for about 18 hours. The lithium carboxylate salt was filtered, suspended in water (100 mL) and acidified with HCl (conc). Filtration and recrystallized from methanol gave 5 2.2 g (75%) as a beige solid, mp 221°–223° C. IR (KBr, cm$^{-1}$) 3432, 3068, 1740, 1604, 1584, 1484, 1444, 1210, 1074, 764, 692. $^1$H NMR (300 MHz, DMSO-d$_6$) δ4.74 (2H, s), 7.07 (1H, d, J=8.0 Hz), 7.44 to 7.68 (11 H, Br.s), 7.82 (1H, d, J=7.3 Hz), 8.03 (1H,s), 8.69 (1H, s), 13.06 (1H, Br.s). $^{13}$C NMR (75 MHz, DMSO-d$_6$) ppm 64.71, 113.68, 116.17, 120.01, 123.45, 126.68, 127.57, 127.91, 128.58, 128.86, 129.09, 129.34, 129.96, 131.58, 135.74, 145.38, 149.30, 151.85, 153.95, 157.87, 170.00 m/e 439 (MH+).

Anal. Calcd. for C$_{26}$H$_{18}$N$_2$O$_5$·0.5 H$_2$O: C, 69.79; H, 4.28; N, 6.27; H$_2$O, 2.01%.

Found: C, 69.53; H, 4.12; N, 6.18; H$_2$O, 0.38%.

EXAMPLE 5

Methyl[4-[4,5-(Diphenyl-2-oxazolyl)-5-oxazolyl]phenoxy] acetate, (7)

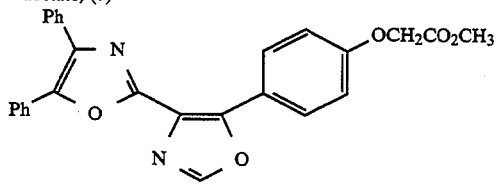

To a mixture of 4,5-diphenyl-2-oxazolyl-methylisocyanide (4) (2.0 g, 7.7 mmol), 4-(methoxycarbonyl)methoxy]benzoic acid (1.6 g, 7.4 mmol) dissolved in DMF (80 mL) was added DBN (3.5 mL, 23.1 mmol) followed by dropwise addition DPPA (1.7 mL, 7.7 mmol). The reaction mixture was stirred about 18 hours, and diluted with sodium bicarbonate solution (1 vol), and extracted with ethyl acetate/ether (1:1). The organic phase was washed with water and brine before drying over MgSO$_4$. Concentration and chromatography (elution with 3% ethyl acetate/chloroform) gave 7 1 g (30%), mp 114°–116° C. IR (KBr, cm$^{-1}$) 3440, 3068, 2952, 1762, 1738, 1608, 1500, 1484, 1442, 1292, 1182, 1070, 836, 764, 694. $^1$H NMR (300 MHz, CDCl$_3$) δ3.84 (3H, s), 4.73 (2H, s), 7.04 to 7.08 (2H, m), 7.33 to 7.46 (6H, m), 7.66 to 7.72 (2H, m), 7.75 to 7.79 (2H,m), 7.98 (1H, s), 8.36 to 8.41 (2H, m). $^{13}$C NMR (75 MHz, CDCl$_3$) ppm 52.33, 65.16, 114.56, 120.92, 123.08, 126.85, 127.96, 128.22, 128.50, 128.59, 128.62, 128.76, 129.31, 132.23, 136.28, 145.77, 149.37, 150.14, 158.81, 168.93. m/e 453 (MH+).

Anal. Calcd. for C$_{27}$H$_{20}$N$_2$O$_5$·(C$_2$H$_5$)$_2$O: C, 71.16; H, 5.15; N, 5.72%.

Found: C, 71.32; H, 4.87; N, 5.98%.

EXAMPLE 6

4-[4,5-(Diphenyl-2-oxazolyl)-5-oxazolyl]phenoxy]acetic acid, (8)

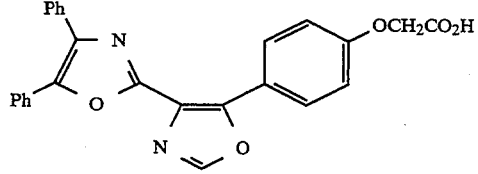

Methyl[4-[4-(diphenyl-2-oxazolyl)-5-oxazolyl]phenoxy]acetate (7) (60 mg, 1.3 mmol) was dissolved in methanol (60 mL) and 5M NaOH solution (6 mL) was added. The reaction mixture heated at reflux for about 18 hours, diluted with water (1 vol), and concentrated to remove solvent. After washing with ether, the aqueous phase was acidified with HCl (conc). Filtration and recrystallization (methanol) gave 8 300 mg (55%) as a beige solid, mp 257°–259° C. IR (KBr, cm$^{-1}$) 3436, 3058, 2912, 1750, 1604, 1500, 1184, 1070, 692. $^1$H-NMR (300 MHz, DMSO-d$_6$) δ4.82 (2H, s), 7.14 (2H, d, J=8.6

Hz) 7.43 to 7.50 (6H, m), 7.61 (2H, d, J=7.6 Hz), 7.69 (2H, d, J=7.6 Hz), 8.28, (2H, d, J=8.6 Hz), 8.66 (1H, s), 13.13 (1H, Br.s). $^{13}$C NMR (75 MHz, DMSO-d$_6$) ppm 64.59, 114.78 , 119.68, 122.04, 126.68, 127.62, 128.03, 128.62, 128.92, 129.15, 129.33, 131.73, 135.69, 145.20, 149.84, 151.37, 154.27, 159.14, 170.01. m/e 439 (MH+).

Anal. Calcd. for C$_{26}$H$_{18}$N$_2$O$_5$: C, 71.22; H, 4.14; N, 6.32.

Found: C, 71.01 ,; H, 4.14; N, 6.39.

EXAMPLE 7

Ethyl[3-[4,5-(diphenyl-2-oxazolyl)-5-oxazolyl]phenoxy]acetate, (9)

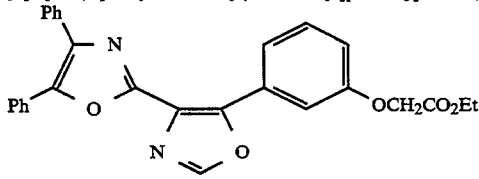

The reaction was performed as above on 4,5-Diphenyl-2-oxazolylmethylisocyanide (4) (2.0 g, 7.7 mmol), 3-[(ethoxycarbonyl) methoxy]benzoic acid (1.7 g, 7.7 mmol) to obtain after chromatography (elution with 5% ethyl acetate/chloroform) 9 1.5 g (42%), mp 51°–54° C. IR (KBr, cm$^{-1}$) 3442, 3064, 2980, 1754, 1586, 1482, 1442, 1198, 1078, 768, 692. $^1$H NMR (300 MHz, CDCl$_3$) δ1.25 (3H, t, J=7.2 Hz), 4.23 (2H, q, J=7.2 Hz), 4.66 (2H, s), 7.03 to 7.06 (1H, m), 7.34 to 7.44 (7H, m), 7.68 to 7.77 (4H, m), 7.89 to 7.92 (1H, m), 8.00 (1H, s), 8.28 (1H, Br.s). $^{13}$C NMR (75 MHz, CDCl$_3$) ppm 14.05, 61.20, 65.36, 113.21, 117.04, 120.53, 124.22, 126.76, 127.96, 128.17, 128.26, 128.35, 128.47, 128.56, 128.74, 129.64, 132.11, 136.32, 145.89, 149.64, 149.83, 154.08, 157.78, 168.49. m/e 467 (MH+).

Anal. Calcd. for C$_{28}$H$_{22}$N$_2$O$_5$: C, 72.09; H.4.75; N, 6.01.

Found: C, 71.73; H, 4.66; N, 5.98.

EXAMPLE 8

2-[5-[3-(Methoxymethoxy)phenyl]-4-oxazolyl]-4,5-diphenyloxazole, (10)

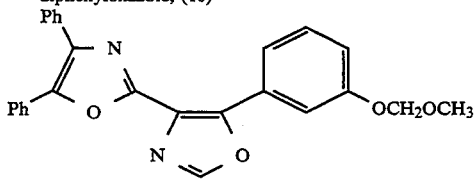

The reaction was performed on 4,5-diphenyl-2-oxazolyl-methylisocyanide (4) ( 2.85 g, 11 mmol), 3-[(methoxy)methoxy]benzoic acid (2.0 g, 11 mmol) to obtain after chromatography (elution with 5% ethyl acetate/chloroform) 10 2.5 g (58%) as an oil. IR (KBr, cm$^{-1}$) 3066, 2956 1604 1582 1482 1444, 1242, 1152, 1080, 988, 766, 694. $^1$H NMR (300 MHz, (CDCl$_3$), δ3.46 (3H, S), 5.22 (2H, s), 7.11 to 7.15 (1H, m) 7.34 to 7.45 (7H, m), 7.68 to 7.71 (2H, m), 7.76 to 7.79 (2H, m), 7.94 to 7.97 (1H, m), 8.01 (1H, s), 8.20 (1H, Br.s). $^{13}$C NMR (75 MHz, CDCl$_3$) ppm 56.04, 94.32, 115.20, 117.94, 120.90, 124.16, 126.70, 127.99, 128.17, 128.21, 128.26, 128.38, 128.48, 128.55, 128.72, 129.55, 132.12, 136.33, 138.54, 145.83, 149.70, 149.98, 151.69, 154.07, 157.10. m/e 425 (MH+).

Anal. Calcd. for C$_{26}$H$_{20}$N$_2$O$_4$·0.3H$_2$O: C, 72.65; H, 4.84; N, 6.52; H$_2$O, 1.26%.

Found: C, 72.83; H, 4.55; N, 6.80; H$_2$O, 1.32%.

EXAMPLE 9

[3-[4,5-(diphenyl-2-oxazolyl)-5-oxazolyl]phenoxy]acetonitrile, (11)

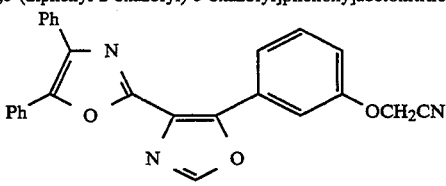

The reaction was performed as above on 4,5-diphenyl-2-oxazolyl-methylisocyanide (4) (3.7 g, 14 mmol), 3-[(cyano)methoxy]-benzoic acid (2.5 g, 14 mmol) to obtain after chromatography (elution with 5% ethyl acetate/chloroform) 11 4.0 g (67%), mp 141°–142.5° C. IR (KBr, cm$^{-1}$) 3368, 3124, 3068, 1586, 1442, 1248, 1052, 872, 766, 694. $^1$H NMR (300 MHz, CDCl$_3$) δ4.71 (2H, s), 7.04 to 7.07 (1H, m), 7.34 to 7.47 (7H, m), 7.68 to 7.74 (4H, m), 7.86 to 7.89 (1H, m), 8.02 (1H, S) 8.74 (1H, Br.s). $^{13}$C NMR (75 MHz, CDCl$_3$) ppm 53.46, 113.02, 114.77, 117.27, 121.17, 124.53, 126.63, 127.98, 128.13, 128.49, 128.54, 128.61, 128.85, 129.95, 132.21, 136.18, 146.02, 149.39, 149.71, 144.01, 156.51. m/e 420 (MH+).

Anal. Calcd. for C$_{26}$H$_{17}$N$_3$O$_3$: C, 74.45; H, 4.09; N, 10.02.

Found: C, 74.44; H, 4.04; N, 10.02.

EXAMPLE 10

5-[3-[4-(4,5-Diphenyl-2-oxazolyl)-5-oxazolyl]phenoxy]methyl-1H-tetrazole, (12)

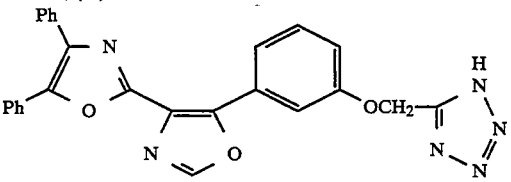

A mixture of [3-[4,5-(diphenyl-2-oxazolyl)-5-oxazolyl]-phenoxy]acetonitrile (11) (900 mg, 2.1 mmol) and tri-n-butyltin azide (791 mg, 2.4 mmol), were heated neat at about 140° C. for about 12 hours. The residue was partitioned between ethyl acetate (200 mL) and 1N HCl solution (100 mL) and stirred for about 2 hours. The organic phase was separated and stirred over 0.1M potassium fluoride solution for about 48 hours, washed with water, brine, and dried. Chromatography (elution with 15% methanol/dichloromethane), and recrystallization from ether gave 12 500 mg (50%) as a yellow solid, mp 215°–217° C. IR (KBr, cm$^{-1}$) 3454, 3142, 3064, 2946, 1614, 1578, 1442, 1238, 1062, 776, 764, 692, 680. $^1$H NMR (300 MHz, DMSO-d$_6$) δ5.52 (2H, s), 7.21 (1H, dd, J=8.2 Hz, J=2.5 Hz), 7.35 to 7.66 (11 H, m), 7.86 (1H, d, J=7.8 Hz), 8.31 (1H, Br.s), 8.71 (1H, s). $^{13}$C NMR (75 MHz, DMSO-d$_6$) ppm 61.27, 115.55, 118.31, 122.16, 125.27, 128.35, 129.20, 129.55, 129.69, 130.26, 130.50, 130.80, 131.07, 131.86, 133.23, 137.40, 147.09, 150.83, 153.62, 155.63, 159.26. m/e 463 (MH+).

Anal. Calcd. for C$_{26}$H$_{18}$N$_6$O$_3$·0.25 H$_2$O: C, 66.88; H, 3.99; N, 18.00; H$_2$O, 0.96%.

Found: C, 66.83; H, 3.85; N, 17.58; H$_2$O, 1.03%.

EXAMPLE 11

5-[3-[(Methoxycarbonyl)methoxy]phenyl]-4-oxazole carboxylic acid, (13)

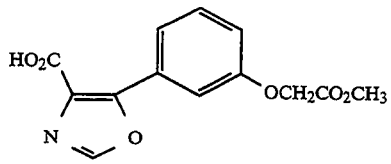

To a solution of benzyl isocyanoacetate (14) (2 g, 11.5 mmol) in THF (25 mL) under N₂ at about −78° C. was added LiHMDS (11.5 mL, 1M in hexanes) dropwise. After about ½ hour, 3-[(methoxycarbonyl)methoxy)-benzoyl chloride (15) (2.8 g, 11.5 mmol) dissolved in THF (50 mL), was added dropwise and the reaction mixture allowed to warm to room temperature and stirred about 5 hour. Saturated ammonium chloride was added (1 vol) and the aqueous phase extracted with diethyl ether. The combined organic layers were washed with brine and dried (MgSO₄). Chromatography (elution with 40% ethyl acetate/hexanes) gave 1.9 g (44%) diester. This material (859 mg, 2.3 mmol) was dissolved in ethyl acetate and added to a suspension of 10% palladium/C (96 mg) in 50 mL of ethyl acetate. The reaction mixture was subjected H₂ (atmospheric pressure) for about 18 hours. Filtration through celite and concentration gave (13) 556 mg (86%), mp 127°–129° C. IR (KBr, cm⁻¹) 3136, 3078, 2922, 2568, 1770, 1702, 1612, 1572, 1436, 1300, 1214, 1090, 1076, 856, 746. ¹H NMR (300 MHz, CDCl₃) δ3.82 (3H, s), 4.72 (2H, s), 7.05 (1H, dd, J=8.1 Hz, 2.1 Hz), 7.41 (1H, t, J=8.1 Hz), 7.76 (1H, d, J=8.1 Hz), 7.90 (1H, Br.s), 8.01 (1H, s). ¹³C NMR (75 MHz, CDCl₃) ppm 52.30, 65.17, 113.97, 117.84, 121.53, 125.91, 127.26, 129.78, 148.75, 155.26, 157.64, 162.94, 169.35. m/e (MH+for $C_{13}H_{12}N_1O_6$): Calcd. 278.0665; Obsd. 278.0656.

EXAMPLE 12

Methyl [3-[4-(4,5-diphenyl-4H-1,2,4-triazol-3-yl)-5-oxazolyl]-phenoxy]acetate, (16)

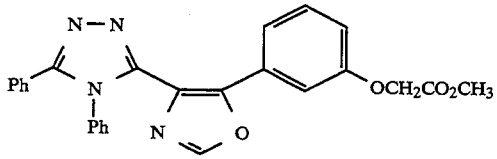

5-[3-[(Methoxycarbonyl)methoxy]phenyl]-4-oxazolecarboxylic acid (13) (460 mg, 1.7 mmol) was dissolved in THF (35 mL) and 4-methyl morpholine (0.2 mL, 1.8 mmol) under N₂ at about 0° C. and i-butyl chloroformate (0.22 mL, 1.7 mmol) added dropwise. The solution was stirred about 1.5 hours and N-phenyl-benzamidrazone (368 mg, 1.7 mmol), dissolved in THF (15 mL), was added dropwise and the reaction mixture stirred about 3 hours at room temperature. The solvent was removed by rotory evaporation and the residue taken up in toluene (50 mL) and washed with water. The solution was heated at reflux under Dean-Stark conditions for about 18 hours, concentrated, and crystallized from diethyl ether to give 16 422 mg (56%), mp 208°–210° C. IR (KBr, cm⁻¹) 3478, 3136, 2956, 1750, 1534, 1498, 1198, 1170, 960, 780, 700. ¹H NMR (300 MHz, CDCl₃) δ3.78 (3H, s), 4.68 (2H, s), 6.96 (1H, dd, J=8.1 Hz, J=2.3 Hz), 7.12 (2H, d, J=6.9 Hz), 7.25 to 7.61 (11H, m), 7.76 (1H, s). ¹³C NMR (75 MHz, CDCl₃) ppm 52.22, 65.19, 112.21, 116.67, 119.91, 126.43, 127.39, 127.99, 128.35 (2C), 128.54, 129.28, 129.73, 129.97, 134.56, 149.30, 157.85. m/e 453 (MH+).

Anal. Calcd. for $C_{16}H_{20}N_4O_4 \cdot 0.1 H_2O$: C, 68.74; H, 4.48; N, 12.33; H₂O, 0.4%.

Found: C, 68.40; H, 4.42; N, 12.29; H₂O, 0.0%.

EXAMPLE 13

[3-[4-(4,5-Diphenyl-4H-1,2,4-triazol-3-yl)-5-oxazolyl]phenoxy]-acetic acid, (17)

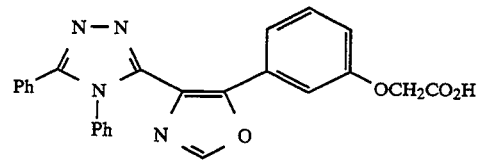

Methyl[3-[4-(4,5-diphenyl-4H-1,2,4-triazol-3-yl)-5-oxazolyl]phenoxy]]acetate (16) (240 mg, 0.53 mmol) was dissolved in DME (27 mL) and lithium hydroxide monohydrate (47 mg, 1.1 mmol) added and the solution heated at reflux for about 18 hours. The lithium carboxylate salt was filtered, suspended in water (5 mL) and acidified with HCl (conc). The product was filtered and washed with water to give 17 165 mg (71%) as a solid, mp 177°–180° C. IR (KBr, cm⁻¹) 3440, 3075, 1740, 1605, 1580, 1500, 1205, 1075, 775, 695. ¹H NMR (300 MHz, CDCl₃) δ4.67 (2H, s), 7.02 to 7.88, (15H, m). ¹³C NMR (75 MHz, CDCl₃) ppm 65.19, 112.00, 117.97, 119.55, 121.78, 125.31, 127.36 (2C), 127.56, 128.49 (2C), 129.34 (2C), 129.46, 129.86, 130.21, 134.01, 148.13, 149.52, 151.73, 154.77, 157.95, 170.84. m/e 439 (MH+).

Anal. Calcd. for $C_{25}H_{18}N_4O_4 \cdot 0.2 H_2O$: C, 65.27; H, 4.47; N, 12.18; H₂O, 5.0%.

Found: C, 65.25; H, 4.06; N, 11.92; H₂O, 6.1%.

EXAMPLE 14

Methyl[3-[4-(4,5-bis(3-thienyl)-2-oxazolyl)-5-oxazolyl]phenoxy]-acetate, (19)

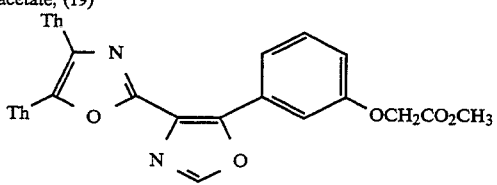

A mixture of 5-[3-[(methoxycarbonyl)methoxy]phenyl]-4-oxazolecarboxylic acid (13) (598 mg, 2.2 mmol), 2-hydroxy-1,2-di-3-thienyl ethanone (18) (484 mg, 2.2 mmol), and DMAP (cat.) was dissolved in THF (10 mL) and DCC (492 mg, 2.4 mmol) was added. The reaction mixture was stirred under N₂ for about 18 hours, filtered, and concentrated. The residue was taken up in acetic acid (12 mL), ammonium acetate (1.15 g, 15 mmol) added, and the solution heated at reflux for about 3 hours. After being diluted with water (1 vol), the solution was extracted into dichloromethane and the organic phase washed with brine and dried (Na₂SO₄). Gradient elution chromatography (5% to 40% ethyl acetate/hexanes) gave 19 231 mg (23%), mp 111°–113° C. IR (KBr, cm⁻¹) 3326, 3118, 3062, 2928, 2850, 1780, 1754, 1626, 1434, 1208, 1078, 854, 780. ¹H NMR (300 MHz, CDCl₃) δ3.79 (3H, s), 4.70 (2H, s), 7.02 to 7.06

(1H, m), 7.36 to 7.45 (5H, m), 7.70 to 7.73 (2H, m), 7.84 to 7.88 (1H, m), 8.00 (1H, s), 8.27 (1H, Br.s). $^{13}$C NMR (75 MHz, CDCl$_3$) ppm 52.17, 65.22, 113.45, 116.67, 120.55, 123.62, 123.80, 125.84, 125.99, 126.24, 127.00, 128.28, 128.82, 129.67, 132.67, 149.67, 153.50, 168.93. m/e 465 (MH+).

Anal. Calcd. for C$_{23}$H$_{16}$N$_2$O$_5$S$_2$: C, 59.47; H, 3.47; N, 6.03.

Found: C, 60.19; H, 4.14; N, 6.63.

EXAMPLE 15

[3-[4-(4,5-Bis(3-thienyl)-2-oxazolyl)-5-oxazolyl]phenoxy]acetic acid, (20)

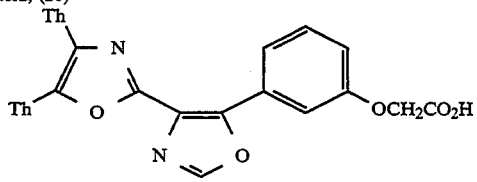

Methyl [3-[4-(4,5-bis(3-thienyl)-2-oxazolyl)-5-oxazolyl]phenoxy]acetate (19) (154 mg, 0.33 mmol) was dissolved in DME (5 mL) and lithium hydroxide monohydrate (31 mg, 0.73 mmol) added, and the solution heated at reflux for about 18 hours. The lithium carboxylate salt was filtered, suspended in water (1 mL) and acidified with HCl (conc). The product was filtered and washed with water to give 20 50 mg (33%) as a tan solid, mp 219°-223° C. IR (KBr, cm$^{-1}$) 3100, 2914, 2524, 1756, 1726, 1584, 1484, 1450, 1242, 1208, 1070, 852, 798. $^1$H NMR (300 MHz, DMSO) δ4.39 (2H, s), 6.75 to 7.86 (11H, m), m/e 451 (MH+).

Anal. Calcd. for C$_{22}$H$_{14}$N$_2$O$_5$S$_2$·0.7 H$_2$O: C, 57.06; H, 3.35; N, 6.05; H$_2$O, 2.7%.

Found: C, 57.05; H, 3.25; N, 6.30; H$_2$O, 1.0%.

EXAMPLE 16

Methyl[3-[4-(4,5 diphenyl-1H-imidazol-2-yl)-5-oxazolyl]phenoxy]acetate, (22)

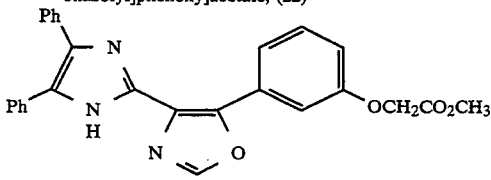

5-[3-[(Methoxycarbonyl)methoxy]phenyl]-4-oxazolecarboxylic acid (13) (343 mg, 1.24 mmol) was dissolved in benzene (8.5 mL) and oxalyl chloride (0.35 mL, 4.0 mmol) added dropwise. The solution was heated at reflux for about 2.5 hours under N$_2$ concentrated, and the residue dissolved in toluene. Palladium (5% on BaSO$_4$) (41 mg), and 2,6-di-t-butyl-4-methylpyridine were added and the solution stirred under an atmosphere of H$_2$ at about 75° C. for about 2.5 hours, filtered through celite, concentrated, and chromatograph (elution with 10% ethyl acetate/chloroform) to give (21) 204 mg (63%). This material (197 mg, 0.75 mmol) was admixed with benzil (159 mg, 0.76 mmol) and ammonium acetate (635 mg, 8.24 mmol) and dissolved in acetic acid (25 mL). The reaction mixture was heated at reflux about 3 hours, diluted with water (1 vol), and extracted into dichloromethane. The organic phase was washed with NaHCO$_3$ solution, brine, and dried (MgSO$_4$). Chromatography (elution with 35% ethyl acetate/hexanes) and recrystallization (chloroform/diethyl ether) gave 22 97 mg 28%, mp 157.5°-158.5° C. IR (KBr, cm$^{-1}$) 3356, 3066, 1752, 1452, 1208, 1192, 1072, 764, 696. $^1$H NMR (300 MHz, DMSO-d$_6$) δ3.65 (3H, s), 4.83 (2H, s), 7.01 (1H, dd, J=8.0 Hz, 2.2 Hz), 7.00 to 7.58 (11H, m), 7.97 (1H, d, J=8.1 Hz), 8.58 (1H, Br.s), 8.65 (1H, s), 12.98 (1H, s). $^{13}$C NMR (75 MHz, DMSO-d$_6$) ppm 53.54, 66.38, 114.91, 116.88, 120.97, 128.37, 123.43 (2C), 128.80, 129.60 (2C), 130.05 (2C), 130.25 (2C), 130.48, 130.52, 131.52, 132.31, 136.63, 138.79, 141.16, 147.60, 152.81, 159.37, 170.72. m/e 452 (MH+).

Anal. Calcd. for C$_{27}$H$_{21}$N$_3$O$_4$: C, 71.83; H, 4.69; N, 9.31.

Found: C, 71.40; H, 4.49; N, 8.97.

EXAMPLE 17

[3-[4-(4,5-Diphenyl-1H-imidazol-2-yl)-5-oxazolyl]phenoxy]acetic acid, (23)

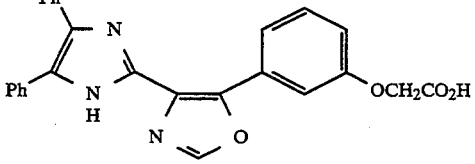

Methyl [3-[4-(4,5-diphenyl-1H-imidazol-2-yl)-5-oxazolyl]phenoxy]acetate (22) (300 mg, 0.66 mmol) was dissolved in methanol (27 mL) and 1M NaOH solution (0.66 mL) was added. The reaction mixture heated at reflux for about 1.5 hours, concentrated to remove solvent, and the residue washed with ether, diluted with water and acidified with HCl to pH=2.9. The solution was filtered and washed with water to give 23 117 mg (40%), mp 237°-240° C. IR (KBr, cm$^{-1}$) 3430, 3186, 3066, 1720, 1604, 1444, 1226, 1212, 766, 696. $^1$H NMR (300 MHz, DMSO-d$_6$) δ4.74 (2H, s), 7.00 (1H, dd, J=8.2 Hz, J=2.1 Hz), 7.19 to 7.58 (11H, m), 8.02 (1H, d, J=7.9 Hz), 8.47 (1H,s), 8.65 (1H,s), 12.97 (1H, s), 13.01 (1H,Br.s). $^{13}$C NMR (75 MHz, DMSO-d$_6$) ppm 64.64, 113.26, 115.05, 119.19, 126.67, 127.06, 127.90, 128.35, 128.54, 128.80, 129.74 130.65, 134.92, 137.04, 139.44, 145.97, 151.08, 157.84, 170.06. m/e (MH+ for C$_{26}$H$_{20}$N$_3$O$_4$): Calcd. 438.1454 Obsd. 438.1464

EXAMPLE 18

Methyl 5-(3-methoxyphenyl)-4-oxazolecarboxylate, (24)

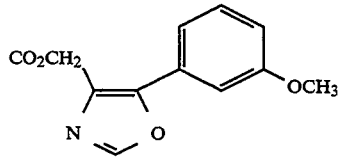

To a mixture of methyl isocyanoacetate (7.1 g, 171 mmol), m-anisic acid (26 g, 171 mmol) and DBN (78 mL, 522 mmol) dissolved in DMF (1.1 L), was added DPPA (37 mL, 171 mmol) by dropwise addition. The reaction mixture was stirred about 18 hours, diluted with 50% saturated ammonium chloride solution (1 vol), extracted with diethylether, and the organic layers washed with water and brine before drying over MgSO$_4$. Concentration and recrystallization (diethyl ether/hexanes) gave 24 23 g (58%), mp 75°-76° C. IR (KBr, cm$^{-1}$) 3110, 3066, 1712, 1604, 1590, 1560, 1516, 1488, 1472, 1456, 1432, 1346, 1314, 1254, 1209, 1170, 1110, 1093, 1036, 892, 850, 786, 646. $^1$H NMR (300 MHz, CDCl$_3$) δ3.84 (3H, s), 3.92 (3H, s), 6.99 (1H, dd, J=8.1 Hz, J=2.1 Hz) 7.36 (1H, t, J=8.1 Hz), 7.63 (1H, m), 7.72 (1H, Br.s), 7.88 (1H, s). $^{13}$C NMR (75 MHz, CDCl$_3$) ppm 52.58, 55.60, 113.66, 116.97, 120.87, 126.66, 127.87, 129.76, 149.08, 155.61, 159.69, 165.54. m/e 234 (MH+).

Anal. Calcd. for C$_{12}$H$_{11}$N$_1$O$_4$: C, 61.87; H, 4.75; N, 5.98.

Found: C, 61.80; H, 4.76; N, 6.01.

EXAMPLE 19

5-[5-(3-Methoxyphenyl)-4-oxazolyl]-3,4-diphenylisoxazole, (25)

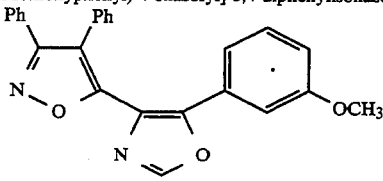

1,2-Diphenylethanone oxime (1.64 g, 7.77 mmol) was dissolved in THF (60 mL), cooled to about −10° C. under N$_2$, and s-butyllithium (13.4 mL of 1.3M in hexanes) added dropwise and the solution was warmed to room temperature. After being stirred about 1 hour, methyl 5-(3-methoxy-phenyl)-4-oxazolecarboxylate (24) (1.65 g, 7.07 mmol) dissolved in 10 mL of the same solvent, was added dropwise and the reaction mixture stirred about 5 hours. Saturated ammonium chloride solution (1 vol) was added, and the solution extracted into chloroform, washed with brine, and dried (MgSO$_4$). Concentration gave 3.05 g of which (2.75 g, 6.89 mmol) was taken up in benzene and p-TsOH (197 mg, 1.03 mmol). The solution was heated at reflux under Dean-Stark conditions for about 1 hour, concentrated onto SiO$_2$ and chromatographed (elution with 15% ethyl acetate/hexanes) gave 25 1.0 g (37.4%) as colorless crystals, mp 146.5°-148° C. IR (KBr, cm$^{-1}$) 3120, 1608, 1578, 1518, 1490, 1464, 1436, 1414, 1350, 1288, 1272, 1212, 1174, 1152, 1114, 1102, 1064, 1054, 972, 936, 888, 832, 788, 770, 706, 696, 666. $^1$H NMR (300 MHz, CDCl$_3$) δ3.78 (1H, s), 6.87 to 6.91 (1H, m), 7.12 to 7.40 (11H, m), 7.46 to 7.49 (2H, m), 7.92 (1H, s). $^{13}$C NMR (75 MHz, CDCl$_3$) ppm 55.51, 111.89, 115.92, 119.25, 123.39, 128.16, 128.55 (2C), 328.76 (2C), 128.88 (2C), 129.28, 129.84, 130.07, 130.20 (2C), 150.25, 150.65, 159.65, 159.80, 162.15. m/e 395 (MH+).

Anal. Calcd. for C$_{25}$H$_{18}$N$_2$O$_3$: C, 76.13; H, 4.60; N, 7.10.

Found: C, 75.88; H, 4.43; N, 6.97.

EXAMPLE 20

3-[4-(3,4-Diphenyl-5-isoxazolyl)-5-oxazolyl]phenol

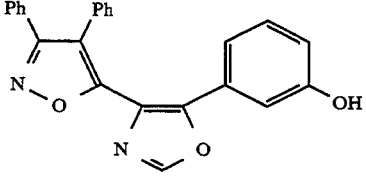

5-[5-(3-Methoxyphenyl)-4-oxazolyl]-3,4-diphenylisoxazole (25) (1.01 g, 2.56 mmol) was dissolved in dichloromethane (65 mL) and cooled to about 0° C. under N$_2$. Boron tribromide solution (13 mL of 1M in dichloromethane) was added dropwise and the solution stirred about 18 hours at room temperature. Methanol (10 mL) was added dropwise {caution: reacts vigorously}, and after being stirred about 10 minutes the solution was concentrated on to SiO$_2$ and chromatographed (elution with 10% ethyl acetate/chloroform) to give the phenol 631 mg (68%), mp 199°-200° C. IR (KBr, cm$^{-1}$) 3240, 3132, 1586, 1514, 1350, 1340, 1218, 1132, 864, 784, 770, 702. $^1$H NMR (300 MHz DMSO-d$_6$) δ6.77 to 6.81 (1H, m), 6.91 to 6.96 (2H, m), 7.11 to 7.15 (2H, m), 7.19 to 7.26 (4H, m), 7.40 to 7.46 (5H, m), 8.58 (1H, s), 9.75 (1H, Br.s). $^{13}$C NMR (75 MHz, DMSO-d$_6$) ppm 112.68, 116.83, 117.03, 118.72, 121.82, 127.26, 128.13, 128.37, 128.43, 128.57, 128.77, 129.67, 129.95, 130.25, 149.71, 151.99, 157.60, 159.37, 161.57. m/e (MH+ for C$_{24}$H$_{17}$N$_2$O$_3$) Calcd. 381.1239, obsd. 381.1238.

EXAMPLE 31

Methyl[3-[4-(3,4-diphenyl-5-isoxazolyl)-5-oxazolyl]phenoxy]acetate (26)

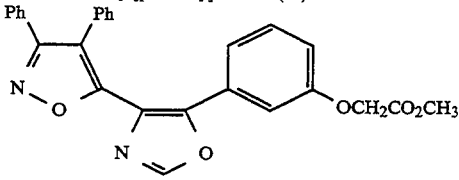

A mixture of 3-[4-(3,4-diphenyl-5-isoxazolyl)-5-oxazolyl]phenol (755 mg, 2.07 mmol), methyl bromoacetate (0.23 mL, 2.43 mmol), potassium carbonate (431 mg, 3.12 mmol), and potassium iodide (cat.) was heated at reflux in acetonitrile (50 mL) for about 18 hours. After being cooled to room temperature, the solution was filtered and concentrated to give a solid, which was recrystallized form methanol to give 26 833 mg (88.9%), mp 132°-135.5° C. IR (KBr, cm$^{-1}$) 3136, 1762, 1426, 1210, 1082, 858, 774, 706. $^1$H NMR (300 MHz CDCl$_3$), δ3.78 (3H, s), 4.62 (2H, s), 6.89 to 6.93 (1H, m), 7.13 to 7.40 (11H, m), 7.46 to 7.49 (2H, m), 7.92 (1H, s). $^{13}$C NMR (75 MHz, CDCl$_3$) ppm 52.56, 65.49, 112.72, 116.48, 119.32, 120.36, 123.62, 128.19, 128.35 (2C), 128.56 (2C), 128.74 (2C), 128.89, 129.24, 129.84, 130.22 (2C), 130.27, 150.32, 158.07, 159.47, 162.19, 169.24. m/e (MH+ for C$_{27}$H$_{21}$N$_2$O$_5$). Calcd. 453.1450, obsd. 453.1457.

EXAMPLE 22

[3-[4-(3,4-Diphenyl-5-isoxazolyl)-5-oxazolyl]phenoxy]acetic acid, (27)

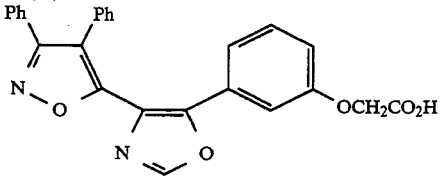

Methyl[3-[4-(3,4-diphenyl-5-isoxazolyl)-5-oxazolyl]-phenoxy]acetate (26) (545 mg, 1.2 mmol) was dissolved in DME (10 mL) and lithium hydroxide monohydrate (2.5 mL, 1M) added and the solution heated at reflux for about 18 hours. The lithium carboxylate salt was filtered, suspended in water and acidified with HCl (conc). The product was filtered and recrystallized from methanol to give 27 242 mg (46%) as a off white solid, mp 76°-90° C. IR (KBr, cm$^{-1}$) 3432, 3132, 3060, 2924, 2554, 1742, 1582, 1438, 1350, 1200, 1076, 770, 698.

$^1$H NMR (300 MHz, DMSO-d$_6$), δ4.67 (2H, s), 6.97 to 7.02 (2H, m), 7.11 to 7.16 (3H, m), 7.24 to 7.26 (3H, m), 7.33 to 7.45 (6H, m), 8.62 (1H, s), 13.07 (1H, Br.s). $^{13}$C NMR (75 MHz, DMSO-d$_6$) ppm 64.55, 112.21, 116.01, 118.75, 119.08, 122.38, 127.43, 128.06, 128.14, 128.43, 128.76, 129.77, 129.95, 130.35, 149.29, 152.21, 157.92, 159.13, 161.71, 169.96. m/e (MH+ for C$_{26}$H$_{19}$N$_2$O$_5$) Calcd. 439.1294, obsd. 439.1292.

EXAMPLE 23

5-(3-Methoxyphenyl)-4-oxazolecarboxamide, (28)

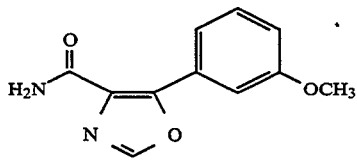

Methyl 5-(3-methoxyphenyl)-4-oxazolecarboxylate (24) (1.76 g, 7.54 mmol) was dissolved in 1,4-dioxane and cooled to about −78° C. in a Parr bomb. Ammonia was condensed for about 2.5 minutes, and the bomb sealed and heated at about 100° C. for about 16 hours. The solution was concentrated onto SiO$_2$ and chromatographed (elution with 15% ethyl acetate/ hexanes) to give 28 1.17 g (71%), mp 162°-163.5° C. IR (KBr, cm$^{-1}$) 3398, 3226, 3108, 1684, 1644, 1612, 1572, 1528, 1492, 1276, 1058, 696. $^1$H NMR (300 MHz, DMSO-d$_6$) δ3.79 (3H, s), 7.00 to 7.03 (1H, m), 7.40 (1H, t, J=8.1 Hz), 7.61 (1H, Br.s), 7.69 to 7.74 (2H, m), 7.97 (1H, Br.s), 8.53 (1H, s). $^{13}$C NMR (75 MHz, DMSO-d$_6$) ppm 55.18, 113.34, 115.65, 119.85, 128.17, 129.32, 129.64, 150.01, 150.89, 159.07, 162.81. m/e 219 (MH+).

Anal. Calcd. for C$_{11}$H$_{10}$N$_2$O$_3$: C, 60.55; H, 4.62; N, 12.84.

Found: C, 60.55; H, 4.54; N, 12.75.

EXAMPLE 24

5-(3-Hydroxyphenyl)-4-oxazolecarboxamide

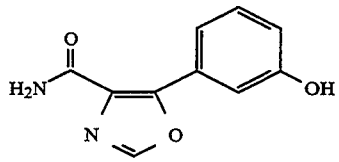

5-(3-Methoxyphenyl)-4-oxazolecarboxamide (1.29 g, 5.9 mmol) was dissolved in dichloromethane (120 mL) and cooled to about 0° C. under N$_2$. Boron tribromide solution (29 mL of 1M in dichloromethane) was added dropwise and the solution stirred about 18 hours at room temperature. Methanol (10 mL) was added dropwise {caution: reacts vigorously}, and after being stirred 10 min the solution was concentrated onto SiO$_2$ and chromatographed (elution with 20% methanol/ethyl acetate) to give the phenol 848 mg (70%), mp 202°-204° C. IR (KBr, cm$^{-1}$) 3398, 3188, 3132, 1684, 1608, 1572, 1254, 1190, 866, 694, 618. $^1$H NMR (300 MHz, DMSO-d$_6$) δ6.82 to 6.85 (1H, m), 7.26 (1H, t, J=8.0 Hz) 7.56 to 7.69 (4H, m), 8.49 (1H, s), 9.66 (1H, s). $^{13}$C NMR (75 MHz, DMSO-d$_6$) ppm 114.62, 116.95, 118.59, 128.08, 129.04, 129.52, 149.27, 151.10, 157.22, 162.80. m/e 205 (MH+).

Anal. Calcd. for C$_{10}$H$_8$N$_2$O$_3$·0.034 H$_2$O: C, 58.65; H, 3.97; N, 13.68, H$_2$O, 0.30%.

Found: C, 58.45; H, 3.76; N, 13.56; H$_2$O, 0.19%.

EXAMPLE 25

Methyl[3-[4-(4,5-diphenyl-2-thiazolyl)-4-oxazolyl]phenoxy]acetate (31)

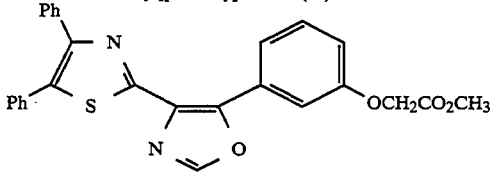

A mixture of 3-[4-(4,5-diphenyl-2-thiazolyl)-4-oxazolyl]phenyl (502 mg, 1.27 mmol), methyl bromoacetate (0.86 mL, 9.08 mmol), potassium iodide (cat.) was heated at reflux in acetonitrile (45 mL) for about 18 hours. After being cooled to room temperature, the solution was filtered, concentrated, and chromatographed (elution with 15% ethyl acetate/hexanes) to give a solid, which was recrystallized from ether to give 31 331 mg (56%), mp 133°-135° C. IR (KBr, cm$^{-1}$) 3058, 1760, 1598, 1438, 1222, 948 852, 760, 686. $^1$H NMR (300 MHz, CDCl$_3$) δ3.73 (3H, s), 4.57 (2H, s), 7.00 to 7.04 (1H, m), 7.29 to 7.43 (9H, m), 7.58 to 7.61 (2H, m), 7.94 (1H, s), 8.01 to 8.04 (1H, m), 8.47 (1H, Br.s). $^{13}$C-NMR (75 MHz, CDCl$_3$) ppm 52.35, 65.61, 113.58, 117.02, 120.83, 128.04, 128.50, 129.00, 129.05, 129.28, 129.83, 130.06, 131.99, 134.76, 135.15, 147.30, 149.40, 150.91, 157.99, 158.96, 169.33. m/e 469 (MH+).

Anal. Calcd. for C$_{27}$H$_{20}$N$_2$O$_4$S$_1$·0.08 H$_2$O C, 69.01; H, 4.32; N, 5.96; H$_2$O, 0.30%

Found: C, 68.82; H, 4.20; N, 5.88; H$_2$O, <0.3%.

EXAMPLE 26

[3-[4-(4,5-Diphenyl-2-thiazolyl)-5-oxazolyl]phenoxy]acetic acid, (32)

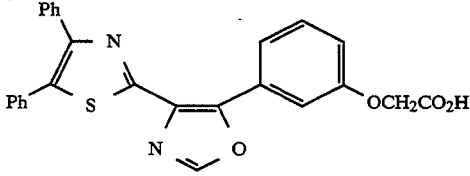

Methyl [3-[4-(4,5-diphenyl-2-thiazolyl) -5-oxazolyl]phenoxy]acetate (31) (223 mg, 0.46 mmol) was dissolved in DME (5 mL) and lithium hydroxide monohydrate (0.7 mL, 1M) added and the solution stirred at about 40° C. for about 18 hours. The lithium carboxylate salt was filtered, suspended in water and acidified with HCl (conc). The product was filtered to give 32 125 mg (60%) as a colorless amorphous solid, mp 240° C. IR (KBr, cm$^{-1}$) 3432, 3060, 1748, 1610, 1436, 1220, 946, 854, 758, 696. $^1$H NMR (300 MHz, DMSO-d$_6$) δ4.56 (2H, s), 7.00 (1H, dd, J=8.2 Hz, J=2.2 Hz), 7.29 to 7.44 (9H, m), 7.54 (2H, d, J=6.9 Hz), 7.99 (1H, d, J=7.8 Hz), 8.13 (1H, Br. s), 8.63 (1H, s). $^{13}$C-NMR (75 MHz, DMSO-d$_6$) ppm 65.82 , 113.79, 115.67, 119.34, 127.99, 128.11, 128.52, 128.75, 129.11, 129.43, 129.61, 131.11, 133.88, 134.13, 146.35, 149.89, 151.43, 158.31, 1.58.36, 170.29. m/e 455 (MH+).

Anal. Calcd. for C$_{26}$H$_{18}$N$_2$O$_4$S$_1$·0.3 H$_2$O: C, 67.88; H, 4.08; N, 6.09 H$_2$O, 1.21%.

Found: C, 67.63; H, 3.80; N, 5.91; H$_2$O, 0.89%.

What is claimed is:

1. The intermediate 4,5-diphenyl-2-oxazolylmethylisocyanide.

2. The intermediate 5-[3-[methoxycarbonyl)methoxy]phenyl]-4-oxazole carboxylic acid.

3. The intermediate 5-(3-hydroxyphenyl)-4-oxazole carboxamide.

* * * * *